(12) United States Patent
Jackson et al.

(10) Patent No.: US 6,171,317 B1
(45) Date of Patent: Jan. 9, 2001

(54) KNOT TYING DEVICE AND METHOD

(75) Inventors: Jasper Jackson, Fort Bragg; Justina A. Franco; Erik K. Walberg, both of San Jose, all of CA (US)

(73) Assignee: Perclose, Inc., Redwood City, CA (US)

( * ) Notice: Under 35 U.S.C. 154(b), the term of this patent shall be extended for 0 days.

(21) Appl. No.: 09/395,947

(22) Filed: Sep. 14, 1999

(51) Int. Cl.⁷ .................................................. A61B 17/04
(52) U.S. Cl. ............................. 606/148; 606/114; 289/17
(58) Field of Search .................................. 606/139, 144, 606/148; 289/17

(56) References Cited

U.S. PATENT DOCUMENTS

| | | | |
|---|---|---|---|
| 5,087,263 | 2/1992 | Li | 606/148 |
| 5,163,946 | 11/1992 | Li | 606/148 |
| 5,217,470 | 6/1993 | Weston | 606/148 |
| 5,454,820 | 10/1995 | Kammerer et al. | 606/148 |
| 5,454,821 | 10/1995 | Harm et al. | 606/148 |
| 5,728,109 | 3/1998 | Schulze et al. | 606/139 |
| 5,769,862 | 6/1998 | Kammerer et al. | 606/148 |
| 5,776,150 | 7/1998 | Nolan et al. | 606/148 |
| 5,814,069 | 9/1998 | Schulze et al. | 606/228 |

*Primary Examiner*—Gary Jackson
(74) *Attorney, Agent, or Firm*—Townsend and Townsend and Crew LLP

(57) ABSTRACT

A knot tying device comprises a knotting guide which carries a pair of snare cords. Each snare cord comprises a suture capture end and a pull end. The snare cords are carried within the knotting guide in a loose, knotted configuration. By capturing a pair of free suture ends in the suture capture ends of the snare cords, the knotted configuration originally embodied in the snare cords can be transferred to the free suture ends by pulling those ends through the knotting guide.

30 Claims, 15 Drawing Sheets

KNOT TYING DEVICE AND METHOD

BACKGROUND OF THE INVENTION

1. Field of the Invention

The present invention relates generally to medical apparatus and methods. More particularly, the present invention relates to methods, devices, and kits for tying knots in suture used in surgical procedures.

At present, most suture knots used in surgical procedures are tied completely by hand, particularly in open surgical procedures where a surgeon has free access to the tissue site to be surgically closed. A variety of knot tying apparatus have been proposed for use in instances where the surgeon does not have direct access, such as laparoscopic and other minimally invasive procedures. Most prior knot tying devices, however, are useful only for tying relatively simple knots and are often combined with a needle driver or other suturing device, rendering the design of the primary suturing instrument more complicated.

For these reasons, it would be desirable to provide improved knot tying devices, kits, and methods which are useful for tying free suture ends which have been deployed by virtually any known suturing technique. The devices will preferably be capable of imparting both simple and complex knot structures in the suture ends in a repeatable and reliable manner. The devices and methods should be easy to use, even in a surgical environment where the suture to be tied may be covered with blood, tissue debris, and other substances which would render tying difficult. In addition, the devices and kits should be of simple construction, be economical to produce, and be capable of being packaged in small, sterile kits for convenient maintenance in a hospital inventory and subsequent use in the operating room environment. At least some of these objectives will be met by the invention described hereinafter.

2. Description of the Background Art

U.S. Pat. No. 5,217,470, describes a device for forming a "protoknot" in suture by direct passage of one end of the suture through a pre-formed partial knot in another end of the suture. Other suture knotting and tying apparatus are described in U.S. Pat. Nos. 5,814,069; 5,776,150; 5,769,862; 5,728,109; 5,454,821; 5,454,820; 5,163,946; and 5,087,956.

SUMMARY OF THE INVENTION

The present invention provides devices, kits, and methods for transferring a pre-formed or pre-tied knot into a pair of free suture ends. The free suture ends will usually be opposite ends of a single length of suture that has been previously surgically placed by conventional techniques, including both direct manual suturing where the surgeon manipulates a needle and suture directly by hand and remote suturing techniques where a specialized suturing instrument is employed. A particularly preferred use of the present invention will be to tie the free ends of a length of suture which has been placed to close a penetration in a blood vessel located at the end of a tissue tract. Such blood vessel penetrations are formed, for example, to provide access to the femoral artery in the groin by the Seldinger technique.

The devices of the present invention comprise a pair of snare cords, each having a capture end and a pull end. The snare cords are disposed in a knotting guide in a loose knot pattern, typically being held over a number of guide pins or other path-defining structure in the knotting guide. Usually, a first snare cord will be formed in a partial knot pattern and a second snare cord will be formed in a complementary knot pattern so that the two cords together are configured as a full knot, although in a loose fashion so that each of the snare cords can be pulled through the knotting guide. Thus, by capturing the first and second suture ends with the capture ends of the first and second snare cords, respectively, the snare cords may be pulled through the knotting guide sequentially or simultaneously to exchange the suture ends for the snare cords. In this way, the knot pattern which was initially embodied in the snare cords is transferred to the suture ends. After detaching the snare cords and removing the suture knot from the knotting guide, the suture knot can be advanced and tightened over the tissue site which is being sutured in an otherwise conventional manner.

In an exemplary embodiment, the knotting guide comprises a base and a removable cover. Usually, the removable cover is hinged so that it can be selectively opened and closed over the base. A plurality of pins are provided on the base to form paths which can define the partial knot pattern and the complementary knot pattern. A particular embodiment which is illustrated comprises a cluster of pins at one end of the guide and a line of pins extending axially down the guide. A variety of other patterns will also be possible. Additionally, the use of channels, cleats, eye holes, and a variety of other mechanical structures for defining the cord paths could also be employed. The purpose of the knotting guide is to permit the snare cords to be interlaced in a desired knot pattern and to be held in a loose condition so that the cords can subsequently be exchanged with the suture. Any structure which meets these objectives will be useful in the knotting guide of the present invention.

The snare cord can be any filament, multi-filament bundle, wire, or the like, which is capable of being configured into the knot pattern and subsequently pulled or drawn through the knotting guide to effect the suture exchange. Preferred cord materials include polyester, nylon, and polypropylene. The capture end of the snare cord may simply be a loop tied or otherwise formed into the capture end permitting the suture to be threaded through the loop to provide capture. Other more complex structures, including wire eyelets, clips, and the like, could also be used. Whatever the specific structure, the capture end should have a profile and a flexibility which permits it to be drawn through the knotting guide during the suture exchange. The pull end of the snare cord can be unmodified, i.e., simply a free end of the snare cord which is cut off to determine its length. Usually, however, some structure, such as a handle, grip, or the like, will be provided on the pull end to facilitate manual pulling and exchange. It will also be possible to provide automatic mechanisms for pulling the snare cords through the knotting guide, in which cases the pull ends may be fastened or coupled to an automatic pulling mechanism. No such automatic pulling mechanisms, however, are illustrated in the present application.

The snare cords will usually (but not necessarily) be identical in construction and appearance, although they may vary in length depending on the particular knotting pattern. Often, however, it will be desirable to be able to distinguish between the two snare cords (or between multiple pairs of snare cords in certain embodiments as described in detail below). The ability to distinguish among the snare cords can be provided by using different colors, different handle shapes, or the like, as part of the snare cord itself. More usually, however, the snare cords will be distinguished based on indicia present on the device itself. In the exemplary embodiment, one snare cord exits from a proximal portion of the knotting guide while a second cord exits from a side of the knotting guide. Instructions are provided to pull the two snare cords in the desired sequence to effect the knot transfer into the suture.

The devices and methods of the present invention can be used to form a wide variety of surgical knots into suture, including sliding surgeon's knots, a square knot, a capstan knot, a cinch knot, and a reef knot.

The knotting devices of the present invention may optionally be configured to include a "break-away" knot pusher. Most simply, a handle or other shaft structure may be attached to the knotting guide in such a way that it can be selectively detached, usually by simply breaking the shaft at a pre-defined, usually weakened, location. The break-away point of the shaft is positioned so that the loose knot formed by the knotting guide will lie adjacent to a pushing end of the shaft after the knot is formed and the shaft is broken away. The shaft will then be positioned so that it may be pushed or otherwise advanced against the knot to move the knot to a desired location and thereafter tighten the knot. Such knotting devices having integral knot pushers will be particularly useful with the preferred sliding surgeon's knots, where one end of the suture can be manually grasped while the knot is slid in a distal direction away from the end which is being held. Preferably, the knotting device will have the preferred structure described above.

The devices, kits, and methods of the present invention can be used during a wide variety of different surgical procedures. Most simply, they can be used to transfer a knot into suture which has been manually placed to close opposed tissue surfaces. A preferred use, as mentioned above, is in the suturing of subcutaneous blood vessel puncture sites, such as those formed when accessing a femoral artery in the groin. Such procedures are described in U.S. Pat. Nos. 5,417,699; 5,613,974; 5,779,719; 5,527,322; and 5,792,152, the full disclosures of which are incorporated herein by reference. Other exemplary suturing procedures include forming an anastomoses between blood vessels, including end-to-end anastomoses, end-to-side anastomoses, and side-to-side anastomoses; suturing prosthetic devices, such as artificial heart valves, into place; forming knots in sutures which have been placed using laparoscopic and other minimally invasive procedures; endoscopic surgery; and the like.

DESCRIPTION OF THE SPECIFIC EMBODIMENTS

Figure 1:
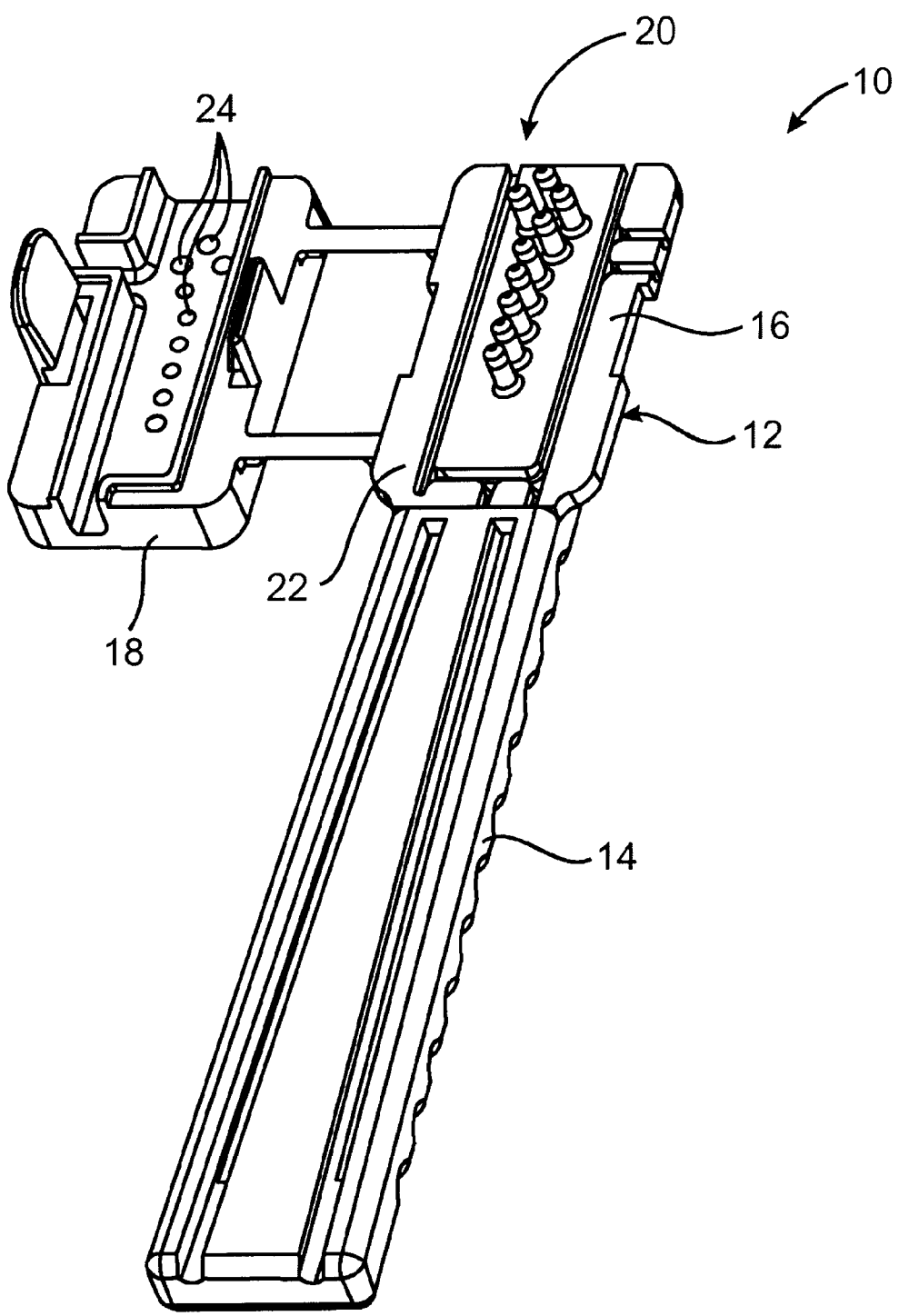
FIG. 1 illustrates an exemplary knotting guide and handle constructed in accordance with the principles of the present invention.
Figure 2:
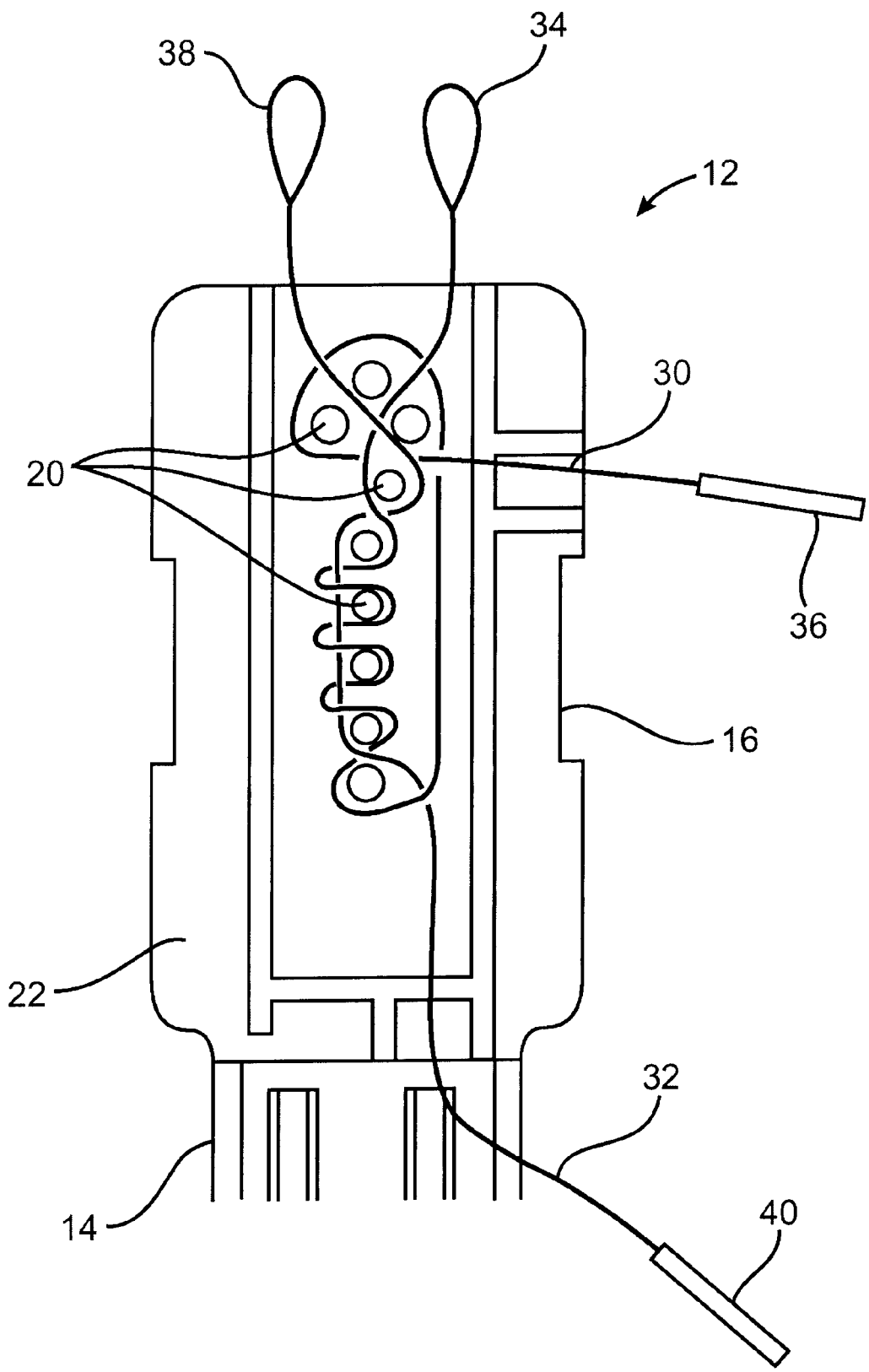
FIG. 2 illustrates the placement of a pair of snare cords in the knotting guide of FIG. 1, where the snare cords are configured to transfer a sliding surgical knot into suture ends according to the method of the present invention.

Referring to FIGS. 1 and 2, a knotting device 10 comprises a knotting guide 12 and a handle 14. The knotting guide 12 includes a base 16 and a cover 18, where the cover may be removably placed over a plurality of pins 20 projecting upwardly from a surface 22 of the base 16. Usually, the cover 18 will include a pattern of holes or receptacles 24 which mate with the pins 20 to form a plurality of enclosed passages between adjacent pins which define paths for configuring, snare cords 30 and 32 (FIG. 2) into a knot pattern, as described in more detail below.

Figure 3A:
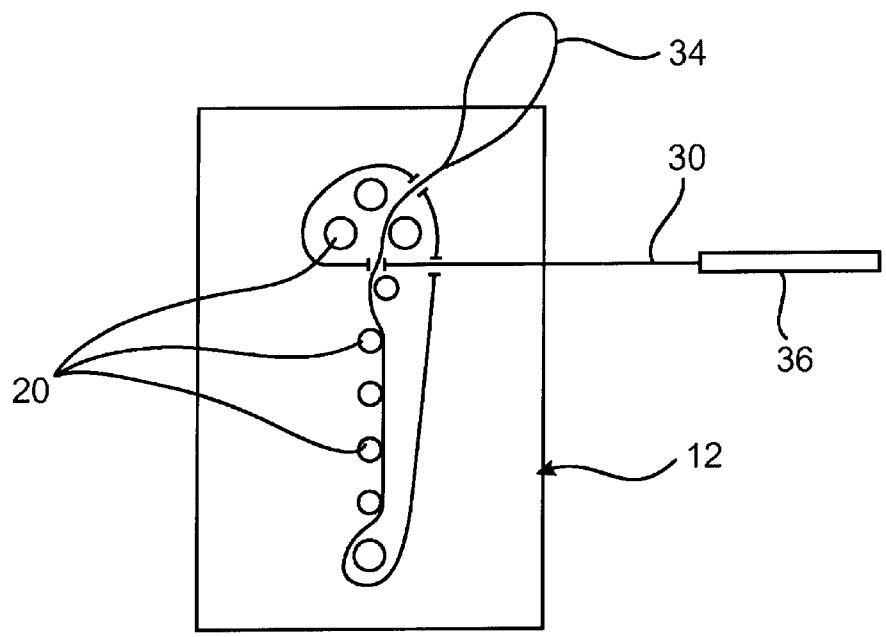
FIGS. 3A and 3B illustrate loading of the snare cords into the knotting guide of FIGS. 1 and 2.
Figure 3B:
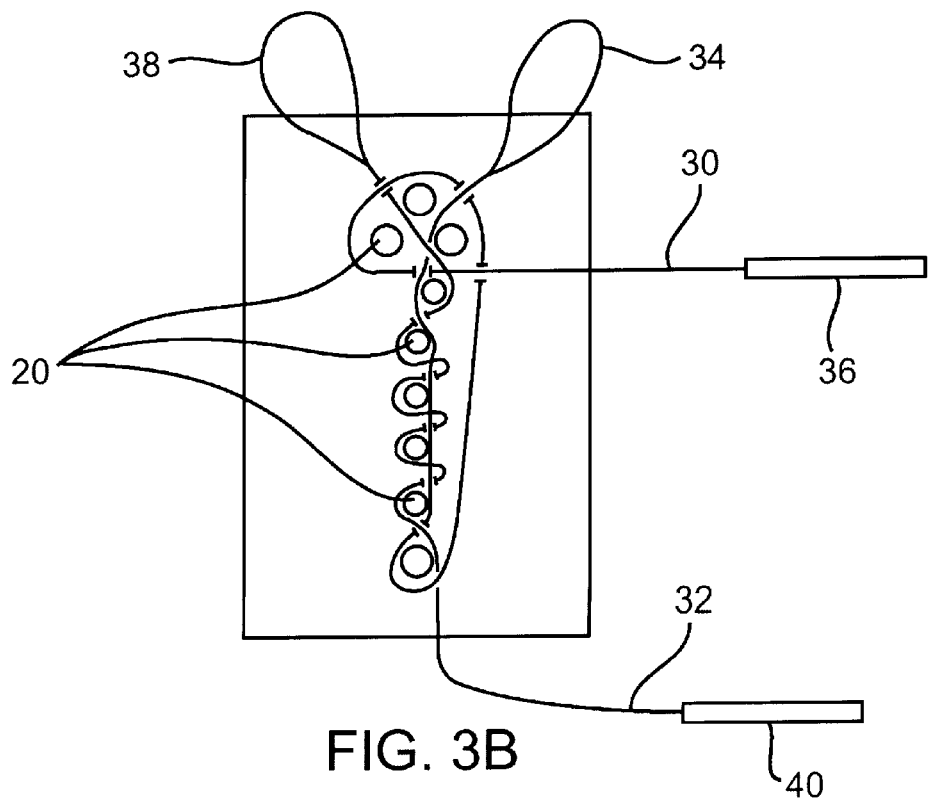
Figure 4:
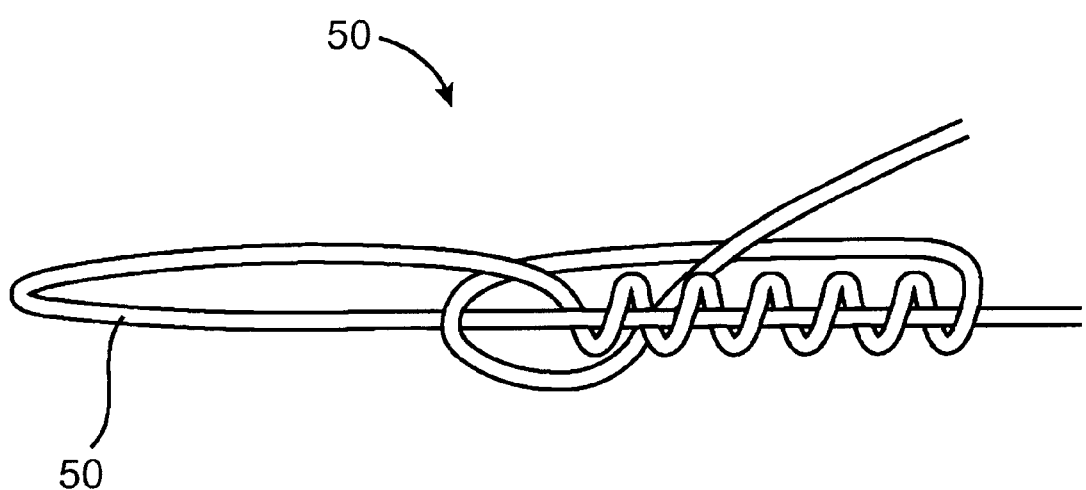
FIG. 4 illustrates the sliding surgical knot which is produced by suture exchange with the knot tying device of FIGS. 1 and 2.

The exact pattern of the pins 20 will be selected based on the type of knot which will be embodied in the snare cord and subsequently transferred into the suture ends. For forming a sliding surgeon's knot in suture, (as illustrated in FIG. 4), the pins 20 may be conveniently formed into a cluster of three or four at one end and a linear array of three, four, five, or more pins arranged axially from the cluster. The snare cords 30 and 32 are first formed into the sliding surgeon's knot as illustrated in FIG. 3A and 3B. For example, the first cord 30 may be formed over the pins with a capture end 34 (e.g., formed into a loop) extending through a pair of pins in the top cluster and a pull end of the cord (comprising handle 36) extending beneath the cluster and out a side of the guide 12, as illustrated in FIG. 3A. The snare cord 30 is illustrated with a solid line indicating that that portion of the cord overlies another portion which is shown in a broken configuration in the drawing. After the first snare cord 30 is placed, the second snare cord 32 (which also comprises a capture end (loop) 38 and a pull handle 40) is threaded over and through the first cord, as illustrated in FIG. 3B. Again, portions of the second snare cord 32 which overlie other portions of either the first cord 30 or second cord, are shown in solid line, while underlying portions are shown in broken line. It will be appreciated that the knot pattern formed in the two snare cords has an identical configuration to the sliding surgeon's knot which is eventually to be formed in the suture ends. The pins 20 are present to hold the snare cords 30 and 32 in their pre-formed or pre-tied configuration and to facilitate pulling the snare coids 30 and 32 through the knotting guide 12 during the suture exchange step which is described below.

Suture exchange may be effected by taking one suture end and passing it through capture loop 34 and the other end and passing it through capture loop 38. The snare cords 30 and 32 may then be pulled through the knotting guide 12 in order to exchange the suture ends for the snare cords, thus imparting the knot pattern into the suture ends. Usually, for the sliding surgeon's knot shown in FIGS. 1 and 2, the first snare cord 30 will be pulled through the knotting guide 12 first, while the second snare cord 32 will be pulled through the knotting guide second. After the snare cords 30 and 32 have been pulled and the suture exchanged, the surgeon's knot 50 illustrated in FIG. 4 will be formed in the suture ends. Note that the surgeon's knot 50 is shown to be formed in a single length of suture where the two suture ends have been pulled through the knotting guide 12. Usually, the surgical suture loop 50 and the knot will have been previously placed in a target suture site, as discussed above.

Figure 5:
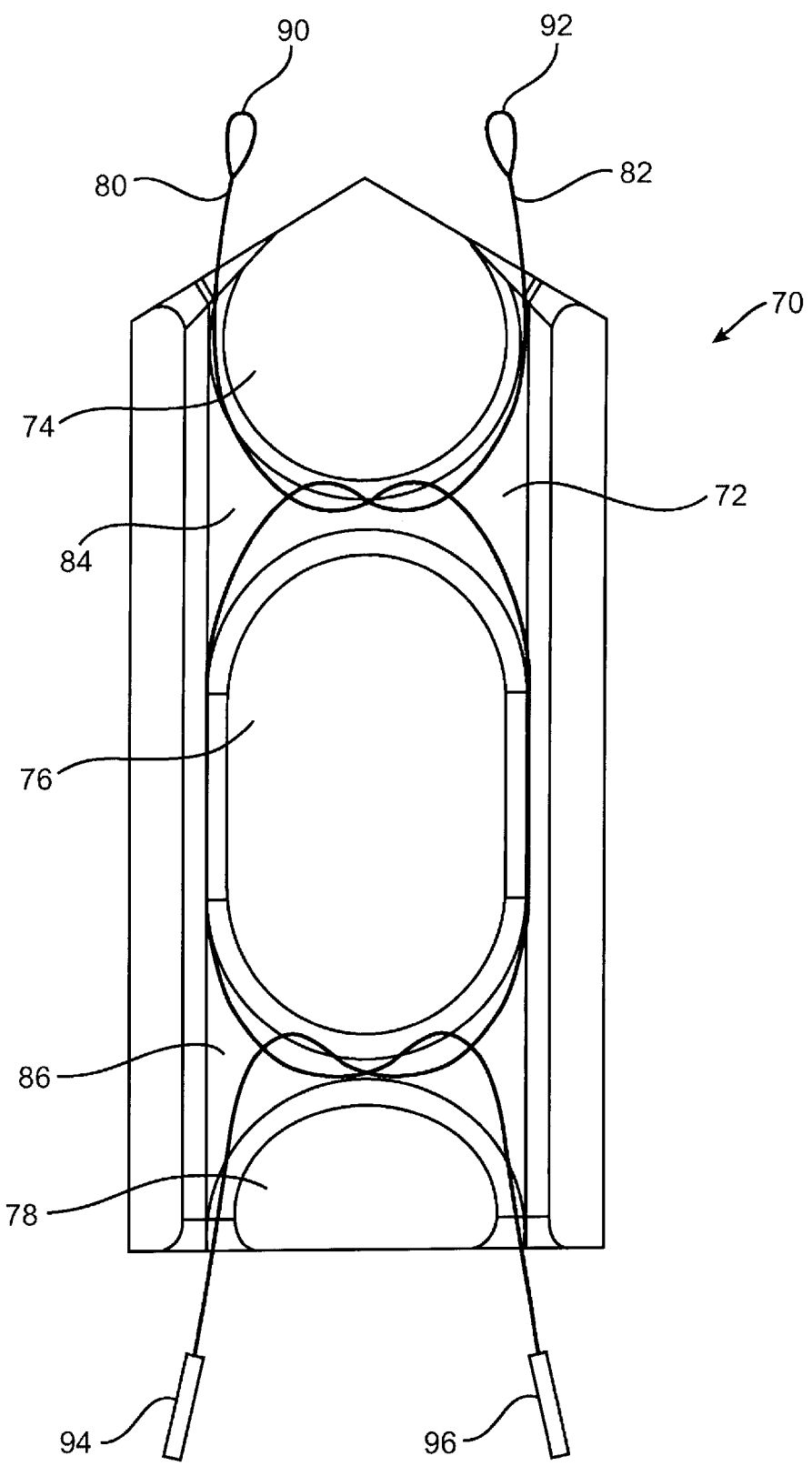
FIG. 5 illustrates an alternative knotting guide pattern suitable for transferring a square knot into a pair of free suture ends.

The principles of the present invention call be applied to a wide variety of surgical knots, including in addition to the sliding surgeon's knot described above, square knots, capstan knots (as described in U.S. Pat. No. 5,217,470, the full disclosure of which is incorporated herein by reference), cinch knots, reef knots, and the like. A knotting guide 70 suitable for transferring a simple square knot into the suture is illustrated in FIG. 5. The knotting guide 70 has a surface 72 with three axially spaced-apart guide posts 74, 76, and 78. The guide posts 74, 76, and 78 are relatively large and have slightly different shapes, and a first snare cord 80 and a second snare cord 82 are threaded over the guide posts as shown. The snare cords 80 and 82 are interlaced into a first square knot 84 between the first and second guide posts 74 and 76 and a second square knot 86 between the second and third guide posts 76 and 78. It should be appreciated that additional guide posts and additional square knots could also be provided. By capturing free suture ends into capture loops 90 and 92 on the first and second snare cords 80 and 82, respectively, the square knot can be transferred into the suture ends by pulling on handles 94 and 96, either simultaneously or sequentially.

Figure 6:
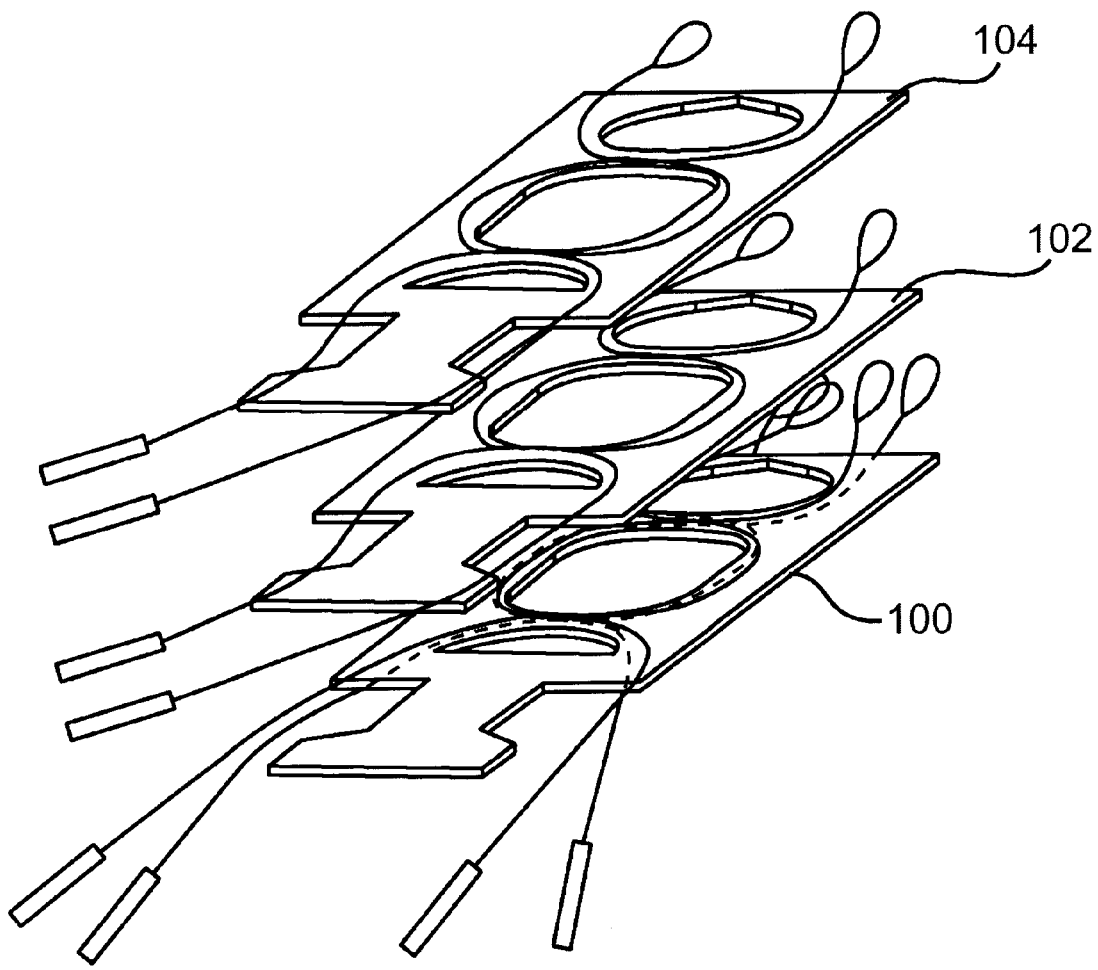
FIG. 6 illustrates the stacking of multiple pairs of snare cords in the knotting guide of FIG. 5.

The knotting guide 70 can be adapted to carrying multiple pairs of snare cords, as illustrated in FIG. 6. There, each of the snare cords is formed into generally the same pattern as shown in FIG. 5, and the multiple snare cords are stacked, preferably with separator plates 100, 102, and 104 between successive snare cord pairs. Thus, four (or more) separate snare cord pairs can be mounted on a single knotting guide 70 using the three separation plates 100, 102, and 104 illustrated in FIG. 6. Snare cord pairs can then be used sequentially, usually beginning at the top with the uppermost separation plate being removed prior to the use of the underlying snare cords of the snare cord pair on top is desirable or necessary since the knot will usually need to be removed prior to the next use of the knotting device.

Figure 7A:
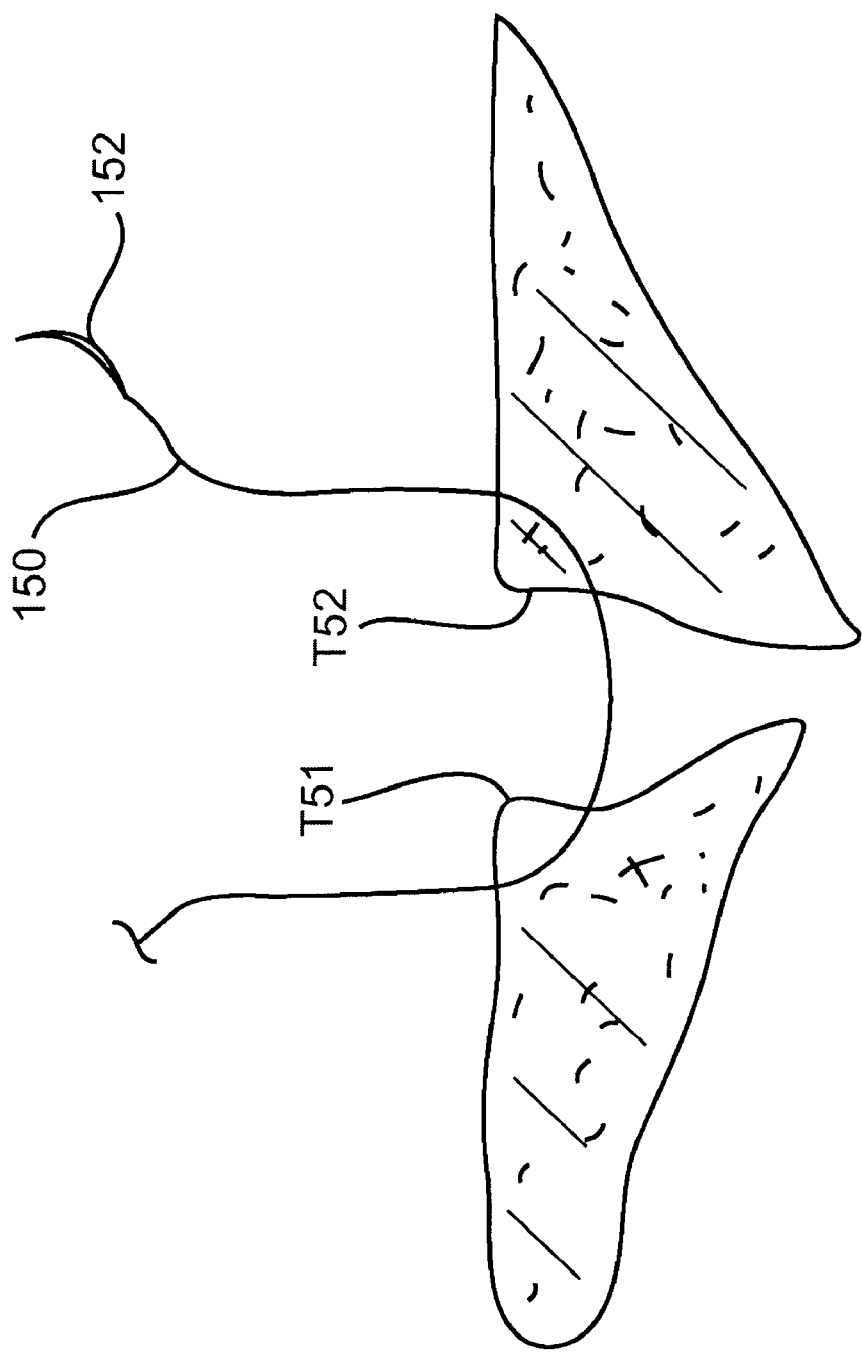
FIGS. 7A through 7E illustrate use of the device of FIGS. 1 and 2 for transferring a knot into suture which has been previously placed using a manual suturing technique.
Figure 7B:
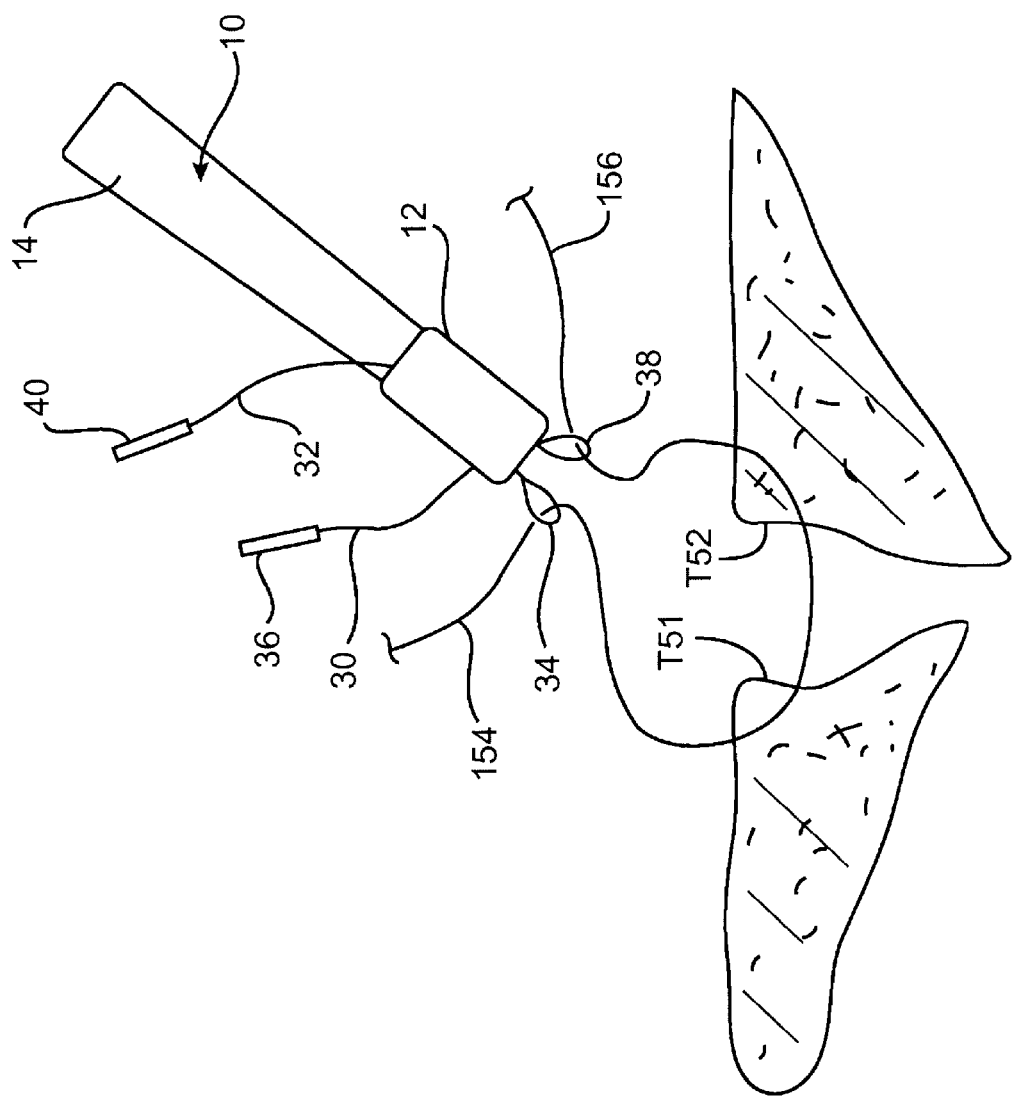
Figure 7C:
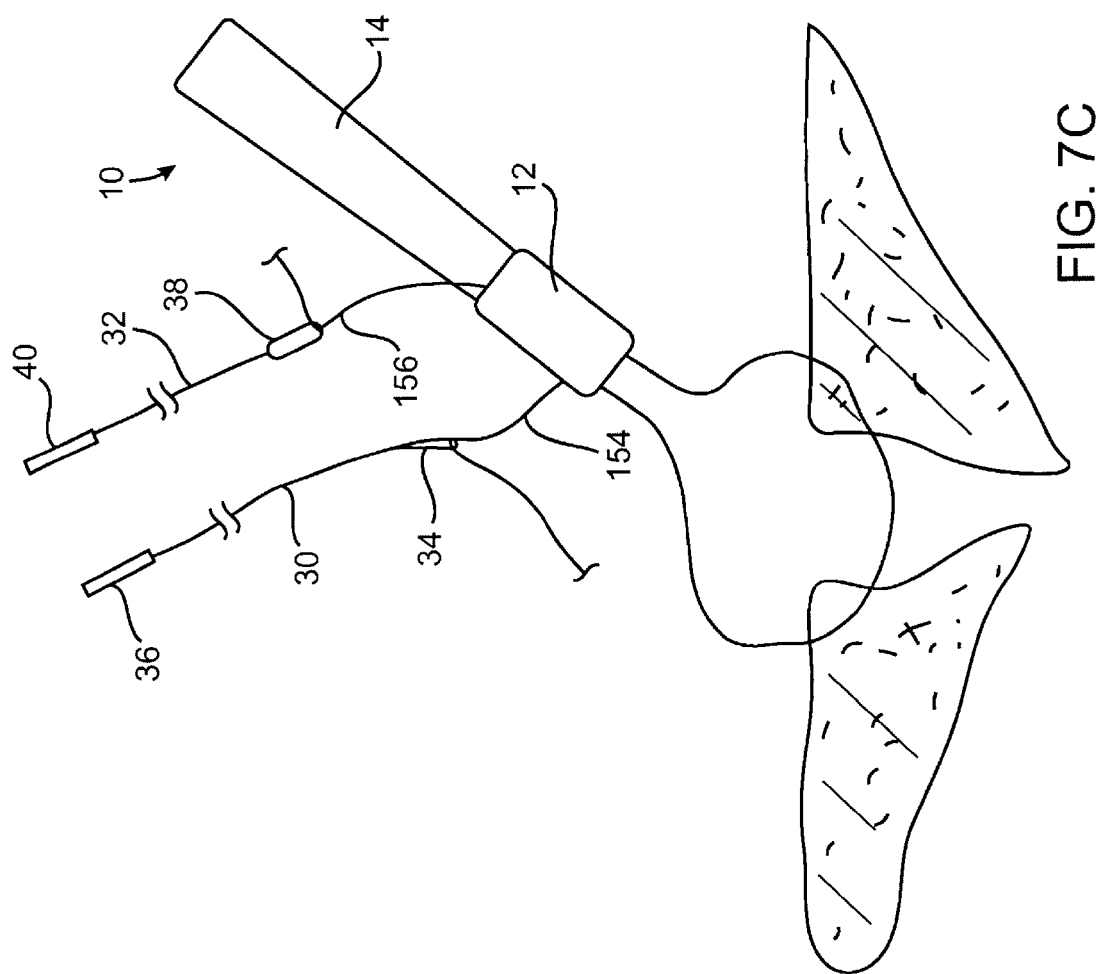
Figure 7D:
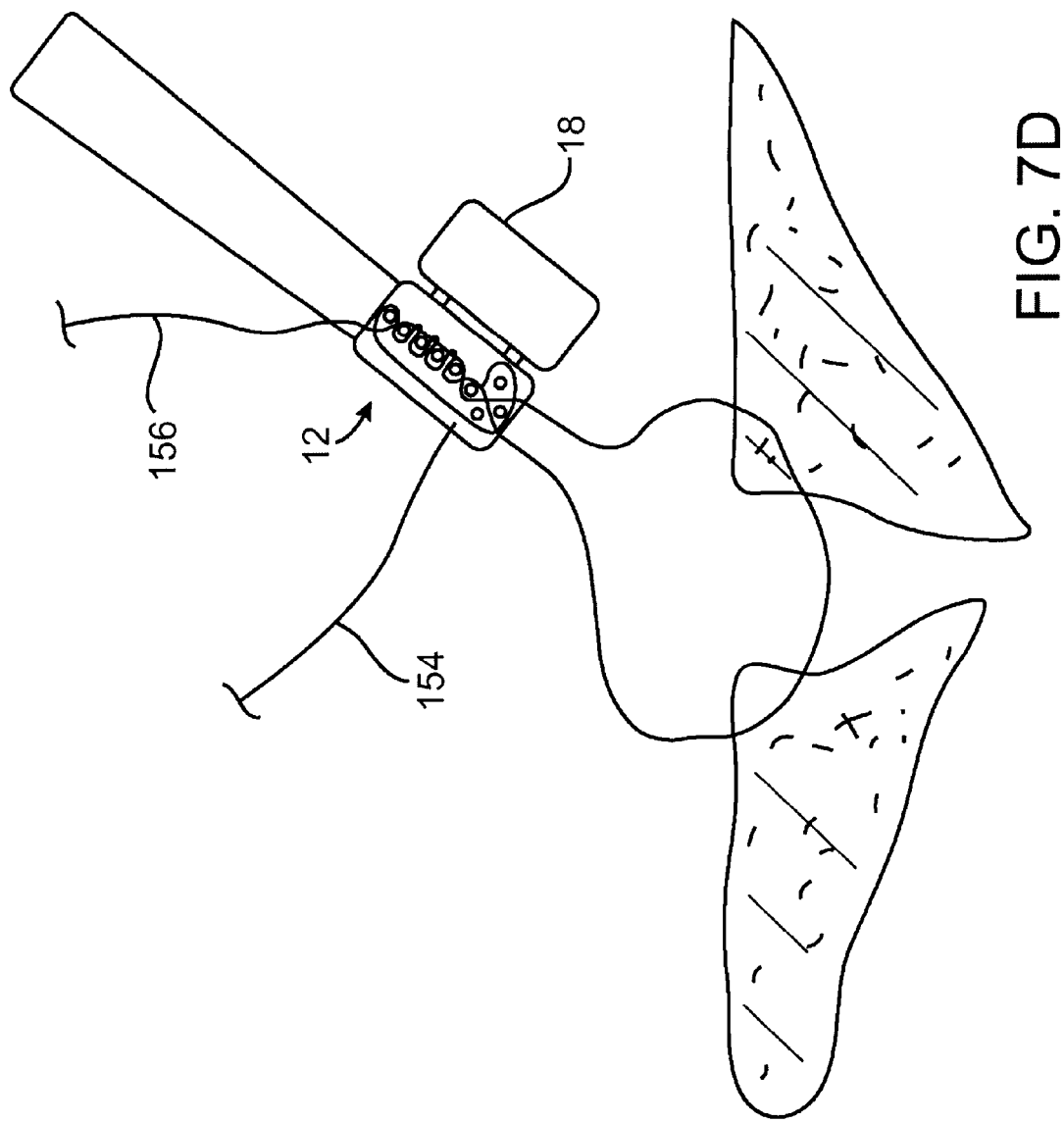
Figure 7E:
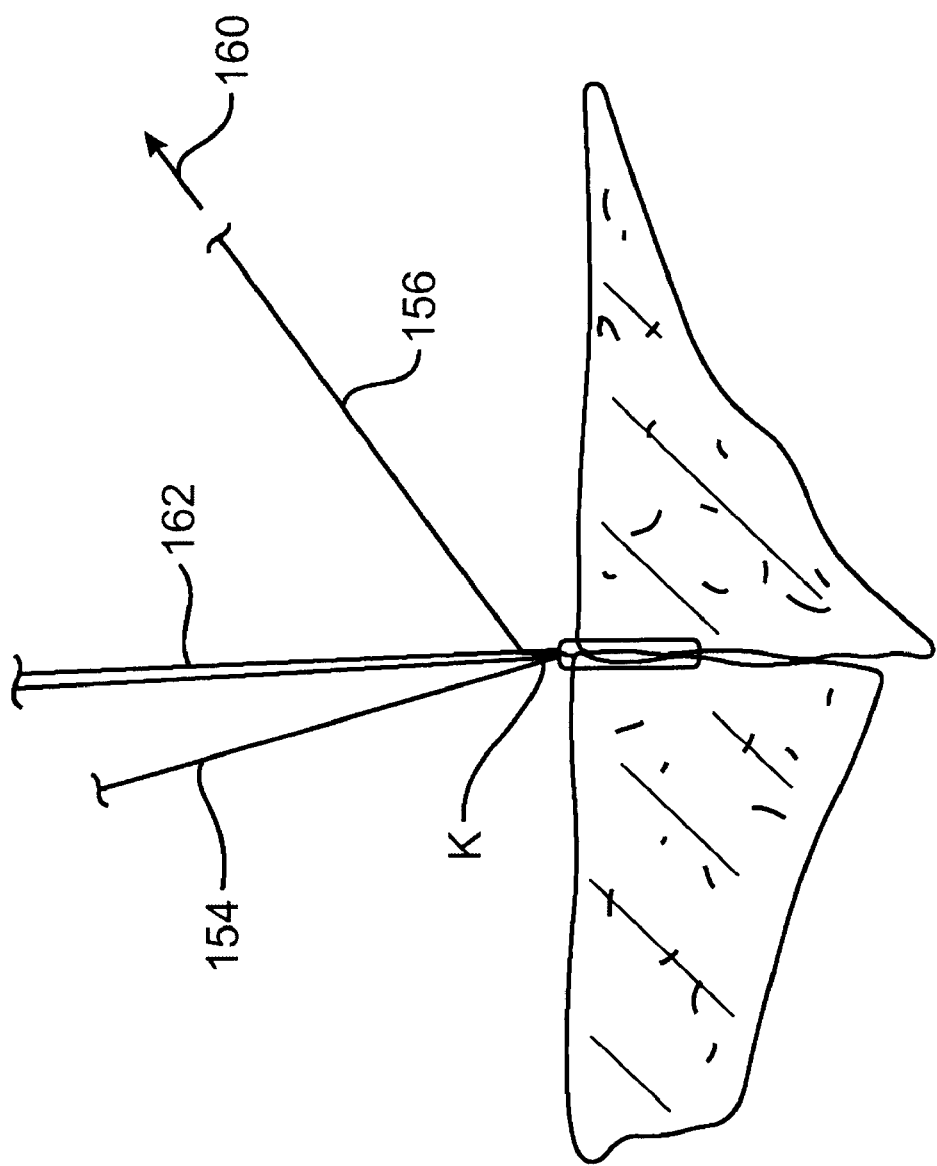

Referring to now FIGS. 7A through 7E, use of the device 10 of the present invention for knotting a pre-deployed length of suture will be described. The suture may be placed at a tissue site by any conventional technique. As illustrated in FIG. 7A, a length of suture 150 having a needle 152 at one end has been manually penetrated through opposed tissue surfaces TS1 and TS2. Prior to tightening the suture to draw the tissue surfaces together, the device 10 of the present invention will be used to transfer or impart a sliding surgeon's knot. First, as shown in FIG. 7B, a first end of the suture 154 is passed through capture loop 34 of the first snare cord 30 and a second suture end 156 is passed through the capture loop 38 of the second snare cord 32. The first snare cord 30 is then drawn through the knotting guide 12 by pulling on the handle 36 until the first suture end 154 emerges from said guide, as illustrated in FIG. 7C. The second snare cord 32 is then drawn through the knotting guide 12 by pulling on the handle 40 until the second suture end 156 also emerges from said guide. The knotting guide 12 may then be opened, typically by flipping cover 18 to uncover the pins, as shown in FIG. 7D. The suture ends 154 and 156 are detached from the snare cords 30 and 32, typically by cutting. The knot which has been imparted in the suture ends 154 and 156 may then be removed from the knotting guide simply by lifting from over the pins, and the knotting device 14 moved away from the suture site 50. The knot is then equivalent in most respects to a hand tied knot (but frequently much better in consistency and quality) and may be tightened by conventional methods depending on the nature of the knot. For the sliding surgeon's knot, the second end (referred to usually as the rail) is manually grasped and tension applied in the direction of arrow 160 (FIG. 7E). The knot K is tightened by pulling on the first suture end 154 and then advanced by pushing it downwardly over the first suture end 156, typically using a knot pusher 162 or other equivalent device.

Figure 8A:
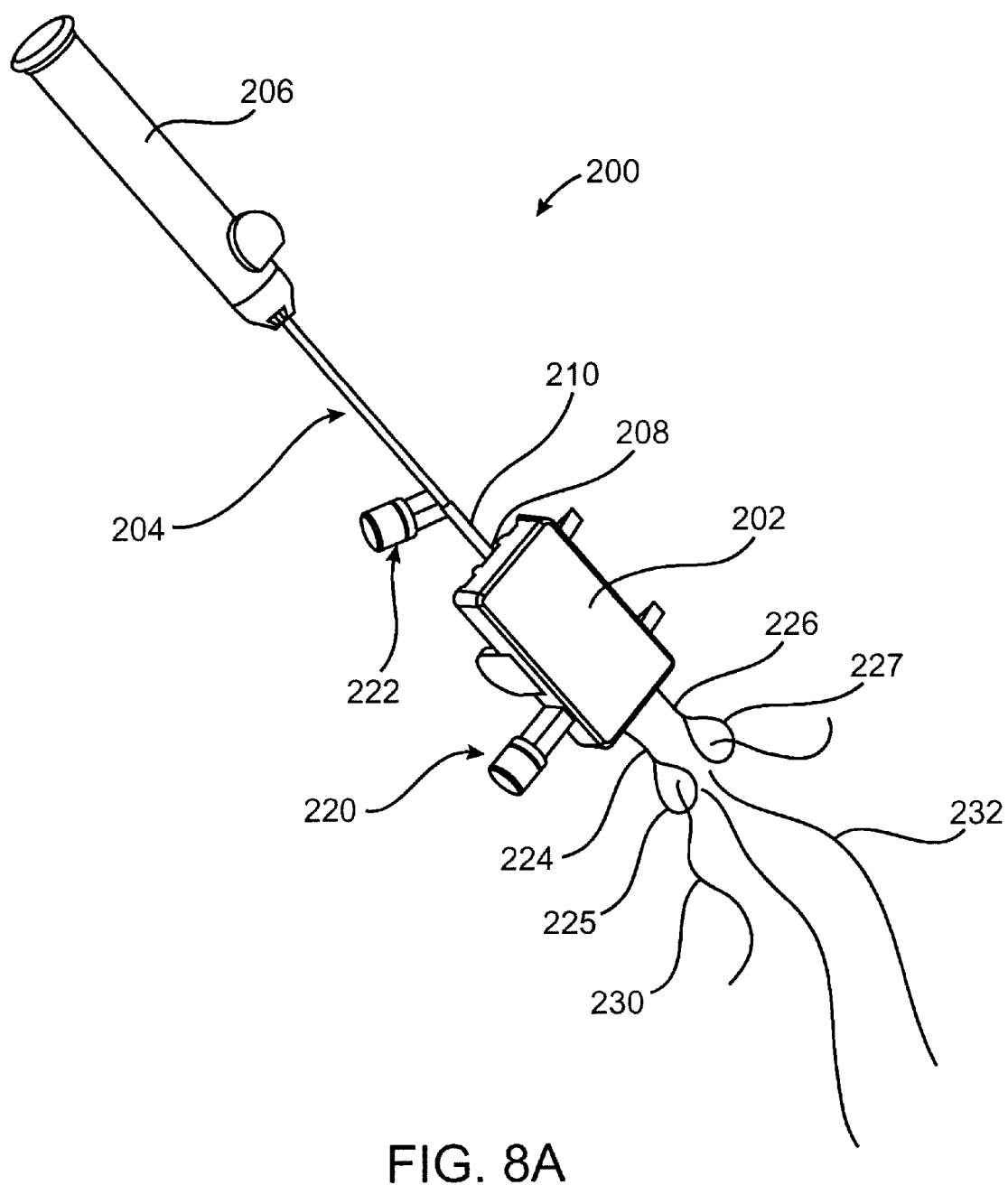
FIGS. 8A through 8C illustrate use of a knotting device having a break-away knot pushing shaft for use in forming and positioning a knot according to the methods of the present invention.
Figure 8B:
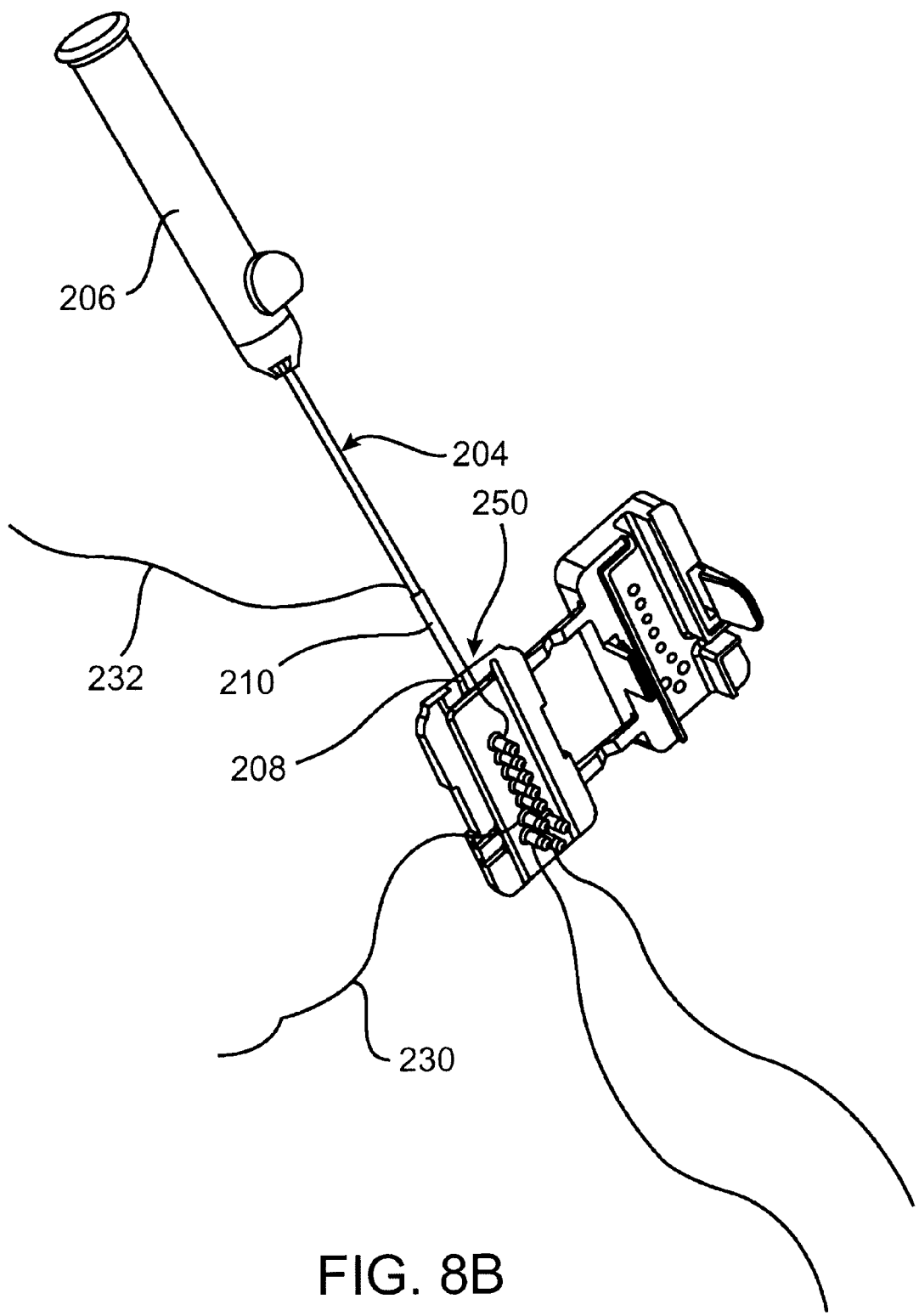
Figure 8C:
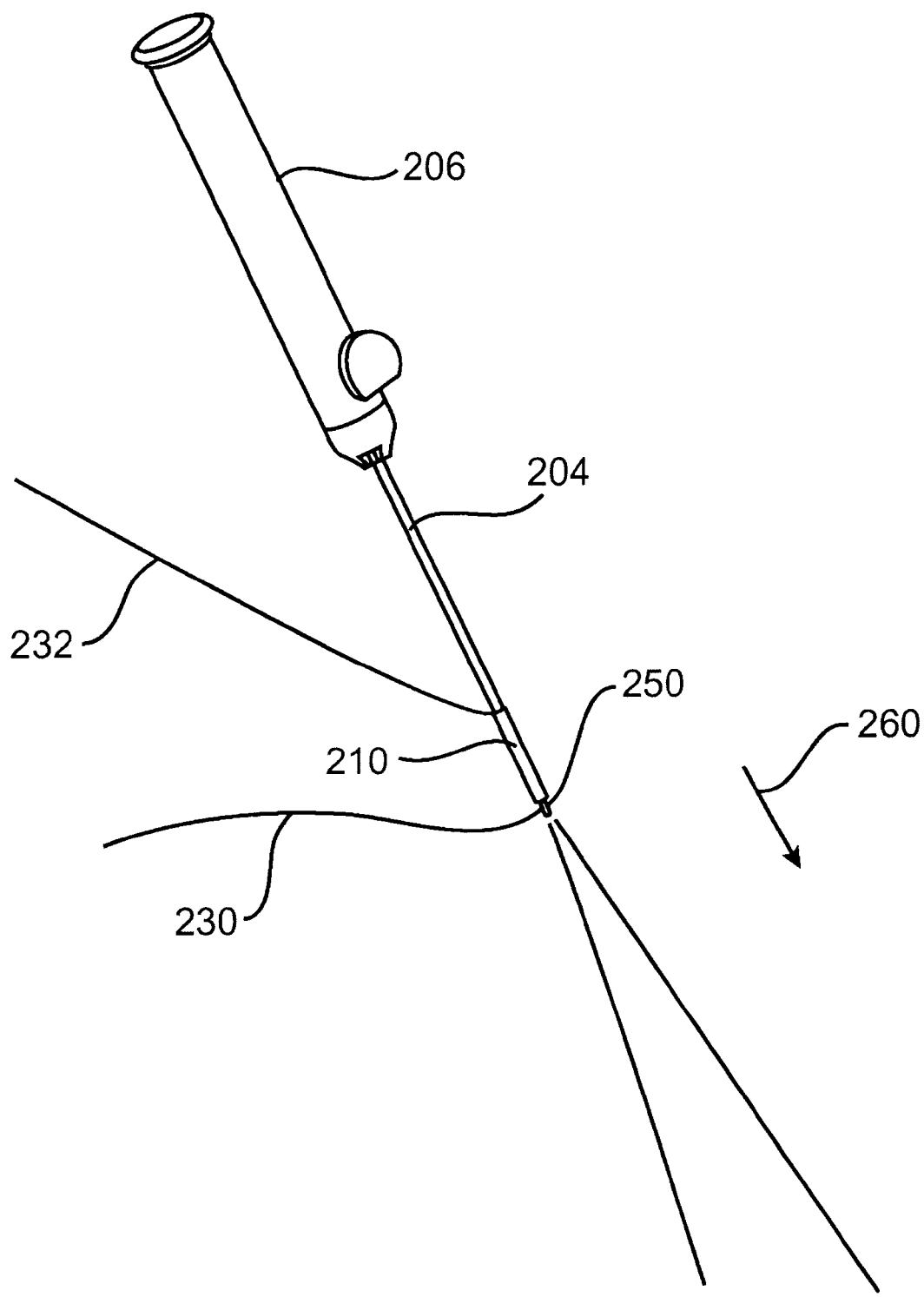

Referring to FIGS. 8A through 8C, the construction and use of a knotting device having an integral knot pusher will be described. The device 200 includes a knotting guide 202 which is constructed virtually identically to the knotting guide 12 of FIG. 1. The device 200, however, includes a break-away shaft 204 having a handle 206, rather than the handle 14 shown in FIG. 1. The break-away shaft 204 has a scored or otherwise weakened location 208 which will preferentially form a clean break from the knotting guide 202 and when the two are broken apart. Pull tabs 220 and 222 are further provided to draw the snare cords 224 and 226, respectively, through the knotting guide 202. End loops 225 and 227 are used to capture suture ends 230 and 232.

Operation of the knotting guide 220 will be the same as that described in the previous embodiments so that, once suture ends 230 and 232 have been snared, and the snare cords 224 and 226 drawn through the guide, a knot 250 (FIG. 8B) will be formed and will lie at the break-away point 208 of the shaft 204. Free suture end 232 will then pass through a lower segment 210 of the shaft while suture end 230 passes out a side of the guide 202, as best shown in FIG. 8B. After opening the suture guide 202, the knot can thus be removed after the shaft is broken from the guide. After cinching the knot, the user can grasp the handle 206, push on shaft 204, to advance the knot distally, i.e., in the direction of arrow 260 in FIG. 8C. The knot can be pushed to remote locations, for example, down a tissue tract in blood vessel suturing, and then tightened to a desired degree by simultaneously pulling on the free ends 230 and 232 of the suture while pushing on the shaft 204.

Figure 9:
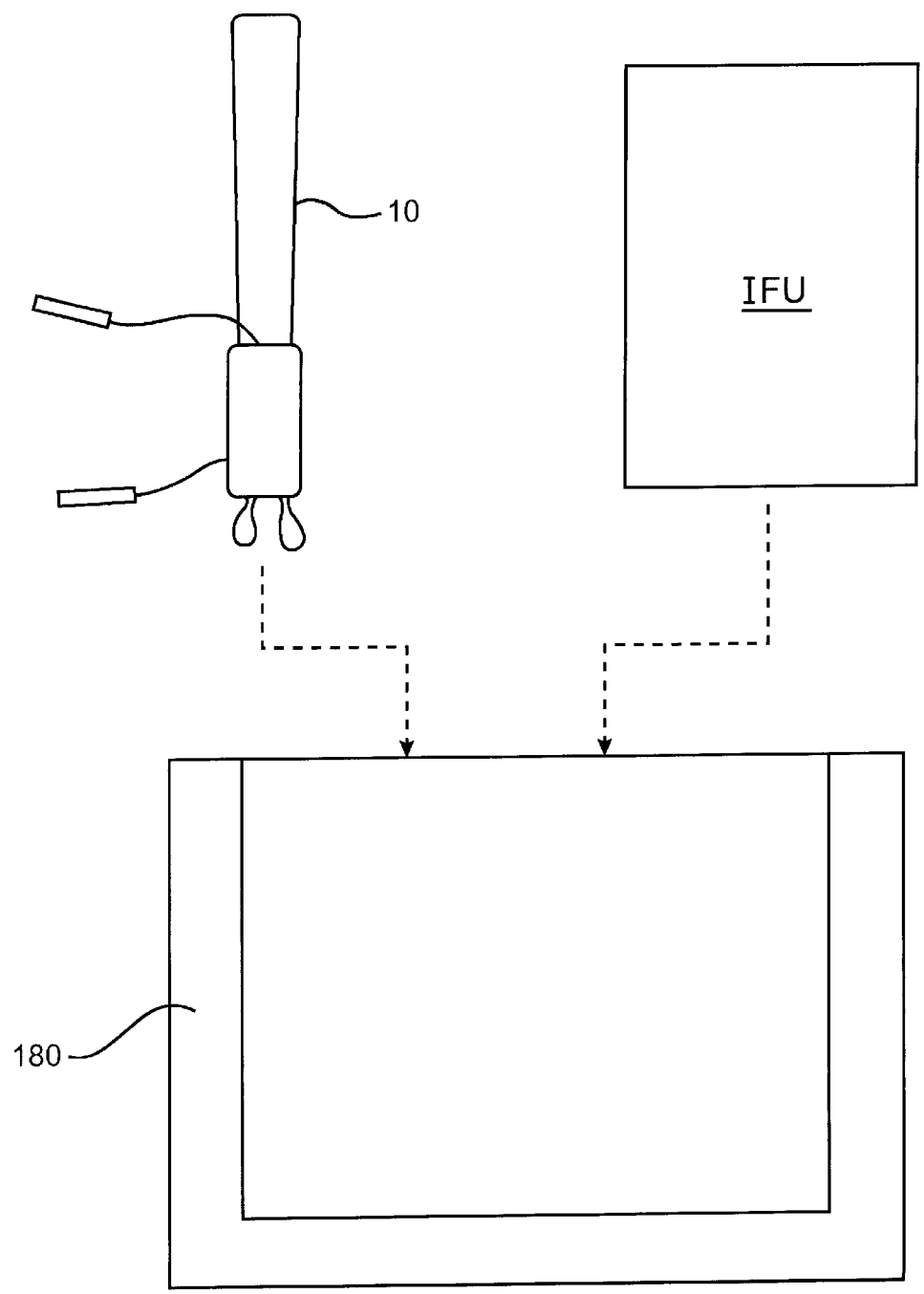
FIG. 9 illustrates a kit comprising a device and instructions for use in a common package according to the present invention.

Referring now to FIG. 9, kits according to the present invention will include a knotting device, such as knotting device 10, which will be maintained sterilely in a conventional package 180, such as a pouch, box, tube, tray, or the like. The package will be sealed to maintain the sterility of the device 10. Usually, instructions for use IFU will also be provided, either as a separate sheet within or otherwise part of the package, or printed in whole or in part of on the packaging. The instructions for use may set forth any of the methods of the present invention described above.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A knot tying device comprising:
    a first snare cord having a capture end and a pull end;
    a second snare cord having a capture end and a pull end; and
    a knotting guide which holds the first snare cord and the second snare cord in a loose knot pattern so that a knot may be formed in a first suture end and a second suture end by capture and exchange with the first snare cord and second snare cord, respectively.

2. A knot tying device as in claim 1, wherein the knotting guide comprises a base and a cover that can be opened to release a knot formed in the suture ends after exchange with the snare cords.

3. A knot tying device as in claim 2, wherein the knotting guide further comprises pins between the base and the cover, wherein the snare cords are arranged about the pins in the loose knot pattern.

4. A knot tying device as in claim 3, wherein the pins are arranged in a pattern having a cluster of four pins at one end and a line of at least three pins extending from the cluster.

5. A knot tying device as in claim 1, wherein the capture end of each snare cord comprises a loop for receiving a suture end therethrough.

6. A knot tying device as in claim 1, wherein the pull end of each snare cord comprises a handle to permit manual grasping thereof.

7. A knot tying device as in claim 1, wherein the knot is selected from the group consisting of a square knot, a sliding surgeon's knot, a square knot, a cinch knot, a capstan knot, and a reef knot.

8. A knot tying device comprising:
   a handle;
   a knotting guide attached to the handle, said knotting guide including a plurality of guide pins arranged in a pre-defined pattern and a cover which can be selectively opened and closed over the pins;
   a first snare cord having a capture end and a pull end arranged over the pins in a partial knot pattern; and
   a second snare cord having a capture end and a pull end arranged over the pins in a knot pattern complementary to the partial knot pattern;
   whereby a knot may be formed in first and second suture ends by capture of the first suture end with the capture end of the first snare cord, capture of the second suture end with the capture end of the second snare cord, pulling of the first snare cord through the pins so that the first suture end assures the partial knot pattern, pulling of the second snare cord through the pins to assure the complementary knot pattern, opening of the cover, and removal of the knot in the suture ends from the knotting guide.

9. A knot tying device as in claim 8, wherein the pins are arranged in a pattern having a cluster of four pins at one end and a line of at least three pins extending from the cluster.

10. A knot tying device as in claim 8, wherein the capture end of each snare cord comprises a loop for receiving a suture end therethrough.

11. A knot tying device as in claim 8, wherein the pull end of each snare cord comprises a handle to permit manual grasping thereof.

12. A knot tying device as in claim 8, wherein the knot is selected from the group consisting of a square knot, a sliding surgeon's knot, a square knot, a cinch knot, a capstan knot, and a reef knot.

13. A kit comprising a knot tying device as in claim 1, and a package, wherein the device is sterile and contained in the package.

14. A kit comprising:
   a knot tying device including:
   a first snare cord having a capture end and a pull end;
   a second snare cord having a capture end and a pull end; and
   instructions for use setting forth the following steps:
   capturing a first suture end with the capture end of the first snare cord;
   capturing a second suture end with the capture end of the second snare end;
   pulling the first snare cord through a path which defines a partial knot pattern; and
   pulling the second snare cord through a path which defines a complementary knot pattern;
   whereby the suture ends are formed into a knot.

15. A method for tying a first suture end and a second suture end into a knot, said method comprising:
   capturing the first suture end with a first snare cord;
   capturing the second suture end with a second snare cord;
   pulling the first snare cord through a path which defines a partial knot pattern; and
   pulling the second snare cord through a path which defines a knot pattern complementary to the partial knot pattern;
   whereby the suture ends are formed into a complete knot.

16. A method as in claim 15, wherein the first suture end and the second suture end comprise opposite ends of a single length of suture.

17. A method as in claim 16, wherein the single length of suture is anchored in tissue.

18. A method as in claim 16, wherein the single length of suture passes through penetrations on the periphery of a blood vessel puncture.

19. A method as in claim 16, wherein the single length of suture passes between blood vessels in an anastomotic attachment.

20. A method as in claim 16, wherein the single length of suture passes between a prosthetic device and tissue.

21. A method as in claim 15, wherein the capturing steps both comprise placing the suture end in a loop formed in the end of the snare cord.

22. A method as in claim 21, wherein the pulling steps both comprise drawing the snare cord through a knotting guide which holds the first snare cord and the second snare cord in a loose knot pattern prior to the pulling steps.

23. A method as in claim 22, wherein the two pulling steps are performed sequentially.

24. A method as in claim 22, wherein the two pulling steps are performed simultaneously.

25. A method as in claim 15, further comprising advancing the complete knot to engage a tissue surface.

26. A method as in claim 15, wherein the complete knot comprises a sliding knot having a rail end and a cinching end, wherein the knot is advanced by holding the rail end and pushing the knot.

27. A method as in claim 15, wherein the complete knot comprises a square knot.

28. A knotting device comprising:
   a knotting guide which imparts a loose knot pattern in a first suture end and a second suture end; and
   a shaft removably secured to the knotting guide, the shaft defining a distal passage for receiving one of the first and second suture ends, wherein said shaft is positioned adjacent to the loose knot after the knot has been formed and the knotting guide has been removed, so that the shaft can be advanced over the one of the first and second suture ends advance the knot along said one of the first and second suture ends.

29. A knotting device as in claim 28, wherein the knotting guide comprises:
   a first snare cord having a capture end and a pull end;
   a second snare cord having a capture end and a pull end; and
   a knotting guide which holds the first snare cord and the second snare cord in a loose knot pattern so that a knot may be formed in a first suture end and a second suture end by capture and exchange with the first snare cord and second snare cord, respectively.

30. A method for tying and advancing a knot to a surgical site, said method comprising:
- capturing first and second ends of a suture loop placed at the surgical site;
- pulling the ends of the suture loop through a knotting guide having a removable shaft, and pulling one of the ends through a passage defined by the removable shaft, wherein a loose knot is formed in the suture ends;
- removing the knotting guide from the shaft to leave the loose knot adjacent to a shaft end; and
- pushing the shaft end along the one of the ends of the suture loop and against the knot to advance the knot against the surgical site.

* * * * *